(12) United States Patent
Bibi

(10) Patent No.: US 6,371,112 B1
(45) Date of Patent: Apr. 16, 2002

(54) DEVICE, SYSTEM AND METHOD FOR PREVENTING COLLAPSE OF THE UPPER AIRWAY

(76) Inventor: Noam Bibi, Sh. Ben Tzion 20/1, 76407 Rehovot (IL)

( * ) Notice: Subject to any disclaimer, the term of this patent is extended or adjusted under 35 U.S.C. 154(b) by 0 days.

(21) Appl. No.: 09/576,872

(22) Filed: May 22, 2000

(51) Int. Cl.[7] .......................................... A61M 11/00
(52) U.S. Cl. .............................. 128/204.18; 128/200.24
(58) Field of Search .......... 128/200.24, 204.18–205.26, 128/207.15, 207.16

(56) References Cited

U.S. PATENT DOCUMENTS

| | | | | |
|---|---|---|---|---|
| 4,821,712 A | * | 4/1989 | Gossett | 128/205.15 |
| 5,243,971 A | * | 9/1993 | Sullivan et al. | 128/205.25 |
| 5,596,983 A | * | 1/1997 | Zander | 128/204.18 |

* cited by examiner

*Primary Examiner*—Glenn K. Dawson
(74) *Attorney, Agent, or Firm*—Mark M. Friedman (57) ABSTRACT

A self contained CPAP device is disclosed. The device includes, a mouthpiece, a breathing tube, an inflatable body and a mask. The mouthpiece is insertable in a mouth of a patient and is attachable to the breathing tube which contains at least one bi-directional valve. The inflatable body functions to adjust an internal cross sectional area of the breathing tube and further serves to regulate air pressure within the patient's mouth. The mask is in fluid communication with the inflatable body and covers the nose of the patient so that exhaled air is routed thereto. Further disclosed is a system for prophylactic treatment of a breathing disorder which includes a sell contained CPAP device. Further disclosed is an improved method of preventing a breathing disorder by means of CPAP. The method includes the steps of inserting a mouthpiece and allowing inhaled air to flow through a bi-directional valve contained within a breathing tube. The method also includes die steps of adjusting an internal cross sectional area of the breathing tube by means of an inflatable body which regulates an, air pressure within the mouth and covering a nose of the patient with a mask communicating which the inflatable body. The mask receives exhaled air and routes it to the nose of the patient.

34 Claims, 6 Drawing Sheets

DEVICE, SYSTEM AND METHOD FOR PREVENTING COLLAPSE OF THE UPPER AIRWAY

FIELD AND BACKGROUND OF THE INVENTION

The present invention relates to a self contained constant pressure applied proximally (CPAP) device and to a system and method which prevent collapse of the upper airway. More particularly, the present invention relates to the use thereof for treatment of breathing disorders including, but not limited to, obstructive sleep apnea (OSA), apnea of infancy (AOI) and sudden infant death syndrome (SIDS).

OSA is a syndrome with significant morbidity and mortality (C. Guilleminault and M. Partinen (eds.) (1990) "Obstructive Sleep Apnea Syndrome: Clinical; Research and Treatment". Raven Press, New York, N.Y., USA, pp xv–xvii). OSA is caused by repeated collapse of soft tissues forming the walls of the upper airway in the sub-glottal region during sleep (C. Guilleminault and M. Partinen, Ibid.). Opening of this portion of the airway depends upon the balance between negative pressure, which is at least –7 or –10 cm $H_2O$ in normal quiet breathing (Levitzki MG (eds)(1986) "Pulmonary Physiology" McGraw—Hill Book Company, New York, N.Y., USA pp 37–40) outside the cavity caused by muscular action during breathing (e.g. action of the diaphragm and muscles surrounding the rib cage) and muscle tone in the upper airway itself (C. E. Sullivan et al., in C. Guilleminault and M. Partinen, Ibid., pp 49–69; S. T. Kuna et al. (1991) JAMA 266:1384–1389; J. E. Remmers et al., (1978) J. Appl. Physiol. 44:931–938; and D. J. Tangel et al. (1991) J. Appl. Physiol. 70:2574–2581). This repeated collapse of the upper airway causes a decrease in blood oxygen saturation which leads to sleep disturbances, fatigue and a general feeling of malaise in affected patients.

OSA is a common disorder with an estimated 2% of women and 4% of men being affected to a degree that treatment is advisable. This means that an estimated 12 to 18 million patients are affected in the USA. Since only about 7 to 18% of the population has been tested for this disorder, these estimates should be viewed as minimum estimates (C. Guilleminault in C. Guilleminault and E. Largesi (eds.) (1983) Raven Press, New York, N.Y., USA, pp 107–125; M. Partinen et al. (1988) Chest 94: 1200–1204; J. JE et al. (1988) Chest 94:9–14; National Commission on Sleep Disorders Research (1995) "Wake Up America: A National Sleep Alert" U.S. Government Printing Office, Washington, D.C., USA, pp 2–10; T. Young et al. (1997) Sleep 20:705–706).

Currently accepted treatment for OSA typically includes continuous positive airway pressure (CPAP). CPAP, as currently practiced, involves connection of a pressurized air delivering device to the mouth or nose of the patient. This device typically is connected to a pressurized air source in the form of a compressor or tank with a regulator. These pressurized air supplies are expensive, large, and noisy.

Delivery of a constant flow of a breathable gas mixture through the device maintains a constant positive pressure in the upper airway. This constantly applied pressure prevents the collapse of the airway described hereinabove(C. E. Sullivan et al. (1981) Lancet 1:862–865; M. H. Sanders et al. (1983) Chest 83:144–145). CPAP is effective in treating OSA by preventing collapse of the airway and associated tiredness, fatigue, diminished intellectual function, and snoring and can even lengthen patient life expectancy (J. Hender et al. (1995) Eur. Respir. J. 8:222–229; H. Minemura et al. (1998) Intern. Med. 37: 1009–1013; C. Jenkinson et al. (1999) Lancet 353: 2100–2105).

In order to keep the pressure in the airway constant during inhalation and exhalation, a pressure valve is sometimes incorporated into the pressurized air delivering device. One such valve is taught by U.S. Pat. No. 4,298,023 for a spring loaded exhalation valve. Teachings of this patent specifically relate to treatment regimens which include a flow of gas delivered to the airway from a pressurized air supply.

However, patient compliance with CPAP treatment regimens is typically poor despite the proven efficacy of the treatment. Research suggests that 60 to 70% compliance is the norm and that the average patient use of CPAP is limited to 5 hours per night (N. P. Kribbs et al. (1993) Am. Rev. Respir. Dis. 147:887–895; H. Rauscher et al. (1993) Chest 103:1675–1680). In addition, many patients never begin treatment at all owing to the high cost of CPAP equipment.

Infants are typically obligatory nasal breathers (Shannon DC In: Disorders of the Respiratory Tract In Children- SIDS and Apnea in infancy Kendig & Chemick eds (1990) W. B. Saunders Company, Philadelphia, Pa., USA pp 939–952.). Any change in airflows in the upper airways increase vulnerability to inadequate ventilation because: (1). the hypopharynx is shallow; (2) the tongue and epiglottis are more cephaled and (3) the mandible is more mobile (Tonkin S.(1975) Pediatrics 55:650–654). Normal infants typically have difficulty responding to nasal occlusion. Studies show that 44% of 6 week old infants struggled but failed to establish an oral airway when the nostrils were pinched for 25 seconds (Swift PGF et al (1973) Arch Dis Child 48:947–950). The physiologic basis for the failure to maintain adequate oral ventilation during occlusion in both normal and at risk infants is unknown. This mechanism has been suggested as a cause of AOI which can lead to SIDS (Anderson R B et al (1971) Biol Neonate 18:395–398.

There is thus a widely recognized need for, and it would be highly advantageous to have, a device, system and method which prevent collapse of the upper airway devoid of the above limitation.

SUMMARY OF THE INVENTION

According to one aspect of the present invention there is provided a self contained CPAP device. The device comprises; (a) a mouthpiece insertable in a mouth of a patient; (b) a breathing tube connecting between an outside environment and an interior of the mouth, the breathing tube containing at least one bi-directional pressure sensitive valve therein; (c) at least one inflatable body, the inflatable body functioning to adjust an internal cross sectional area of the breathing tube during a process of respiration, the inflatable body further serving to regulate an air pressure within the mouth during the process of respiration; and (d) a mask, the mask being in fluid communication with the inflatable body and being designed and constructed to cover a nose of the patient, such that exhaled air is routed thereto.

According to another aspect of the present invention there is provided a system for prophylactic treatment of a breathing disorder, the system comprising a self contained CPAP device, the device being designed and constructed to: (a) maintain sufficient pressure in an upper airway of a patient such that collapse thereof is prevented; and (b) function independently of any item selected from the group consisting of a pump, a compressor, a pressurized gas cylinder and an electro-hydrolytic oxygen source.

According to yet another aspect of the present invention there is provided an improved method of preventing a breathing disorder by means of CPAP, the method comprising the steps of: (a) inserting a mouthpiece in a mouth of a patient; (b) allowing inhaled air to flow through at least one bidirectional pressure sensitive valve contained within a breathing tube connecting between an outside environment and an interior of the mouth; (c) adjusting an internal cross sectional area of the breathing tube during a process of respiration by means of at least one inflatable body, the at least one inflatable body serving to regulate an air pressure within the mouth during the process of respiration and (d) covering a nose of the patient with a mask, the mask being in fluid communication with the at least one inflatable body and being designed and constructed to receive exhaled air therefrom and route the exhaled air to the nose of the patient.

According to further features in preferred embodiments of the invention described below, the at least one inflatable body comprises: (i) at least one elastic balloon; (ii) at least one first additional unidirectional pressure sensitive valve in communication an interior of the breathing tube; and (iii) at least one second additional unidirectional pressure sensitive valve in communication with an exhaled air tube, the exhaled air tube being in communication with the mask;

According to still further features in the described preferred embodiments the at least one inflatable body comprises any number of inflatable bodies having a total inflated volume which is approximately 120 to 350 ml greater than a total deflated volume thereof such that it is suitable for use in adults.

According to still further features in the described preferred embodiments the at least one inflatable body comprises any number of inflatable bodies having a total inflated volume which is approximately 40 to 160 ml greater than a total deflated volume thereof such that it is suitable for use in children. According to still further features in the described preferred embodiments the at least one inflatable body comprises any number of inflatable bodies having a total inflated volume which is approximately 2 to 40 ml greater than a total deflated volume thereof such that it is suitable for use in infants.

According to still further features in the described preferred embodiments the at least one inflatable body comprises any number of inflatable bodies having a total inflated volume which is approximately 2 to 4 ml greater than a total deflated volume thereof for each Kg of mass of said patient.

According to still further features in the described preferred embodiments the inflatable body further comprises at least one undirectional pressure sensitive safety valve in communication with the outside environment, the safety valve functioning to prevent explosion of the at least one inflatable body.

According to still further features in the described preferred embodiments the safety valve opens when a predetermined volume is exceeded.

According to still further features in the described preferred embodiments the mouthpiece is adjustable to fit the mouth of the patient.

According to still further features ID the described preferred embodiments there is provided a mechanism for facilitating inflation of the mouthpiece.

According to still further features in the described preferred embodiments there is provided a mechanism for sealing between the mouthpiece and lips of the patient, such that airflow between the lips and the mouthpiece is diminished According to still further features in the described preferred embodiments the device further comprises a chin holder having a first end which is capable of engaging a chin of the patient and a second end which is connectable to the device.

According to still further features in the described preferred embodiments the breathing tube passes through the mouthpiece According to still further features in the described preferred embodiments the device further comprises at least one retaining piece for holding the device in place.

According to still further features in the described preferred embodiments the at least one retaining piece includes at least one item selected from the group consisting of at least one strap, at least one elastic band, at least one piece of Velcro™ and a pair of protrusions which engage the ears of the patient.

According to still further features in the described preferred embodiments the device further comprises a filter in the breathing tube, the filter designed and constructed to prevent the entry of foreign bodies thereto.

According to still further features in the described preferred embodiments the device is designed and configured for a purpose selected from the group consisting of treating obstructive sleep apnea, treating apnea of infancy and preventing sudden infant death syndrome.

According to still further features in the described preferred embodiments the device comprises: (i) a mouthpiece insertable in a mouth of a patient; (ii) a breathing tube connecting between an outside environment and an interior of the mouth, the breathing tube containing at least one bidirectional pressure sensitive valve therein; (iii) an inflatable body, the inflatable body functioning to adjust an internal cross sectional area of the breathing tube during a process of respiration, the at least one inflatable body further serving to regulate an air pressure within the mouth during the process of respiration; and (iv) a mask, the mask being in fluid communication with the at least one inflatable body and being designed and constructed to cover a nose of the patient, such that exhaled air is routed thereto.

According to still further features in the described preferred embodiments the at least one inflatable body comprises: (i) at least one elastic balloon; (ii) at least one first additional unidirectional pressure sensitive valve in communication an interior of the breathing tube; and (iv) at least one second additional unidirectional pressure sensitive valve in communication with an exhaled air tube, the exhaled air tube being in communication with the mask. This configuration assures that exhaled air passes through the first additional unidirectional pressure sensitive valve, thereby inflating the at least one inflatable body and causing an elevated pressure to form therein and that reducing of the elevated pressure is accomplished by a release of exhaled air through the second additional unidirectional pressure sensitive valve.

According to still further features in the described preferred embodiments there is provided at least one unidirectional pressure sensitive safety valve in communication with the outside environment such that exploding of the at least one inflatable body is prevented by release of the exhaled air through the safety valve when the elevated pressure exceeds a predefined limit.

According to still further features in the described preferred embodiments the method comprises the additional step of adjusting the mouthpiece to fit the mouth of the patient.

According to still further features in the described preferred embodiments the step of adjusting is accomplished by inflating the mouthpiece.

The present invention successfully addresses the shortcomings of the presently known configurations by providing a CPAP device which is small, lightweight, portable, and relies primarily upon exhaled air as a source of pressure.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 4 a, b, and c illustrate airflow through a device according to the present invention during an initial inspiration, an exhalation and all subsequent inhalations respectively.

DESCRIPTION OF THE PREFERRED EMBODIMENTS

The present invention is of a self contained constant pressure applied proximally (CPAP) device and is further of a system and method which prevent collapse of the upper airway which can be used for treatment of breathing disorders Specifically, the present invention can be used to prevent or treat a variety of conditions including, but not limited to, obstructive sleep apnea (OSA), apnea of infancy (AOI) and sudden infant death syndrome (SIDS) and to improve patient compliance with recommended treatment protocols. The present invention is unique because it relies primarily upon exhaled air as a source of pressure.

The principles and operation of a self contained constant pressure applied proximally (CPAP) device and of a system and method which prevent collapse of the upper airway according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 1:
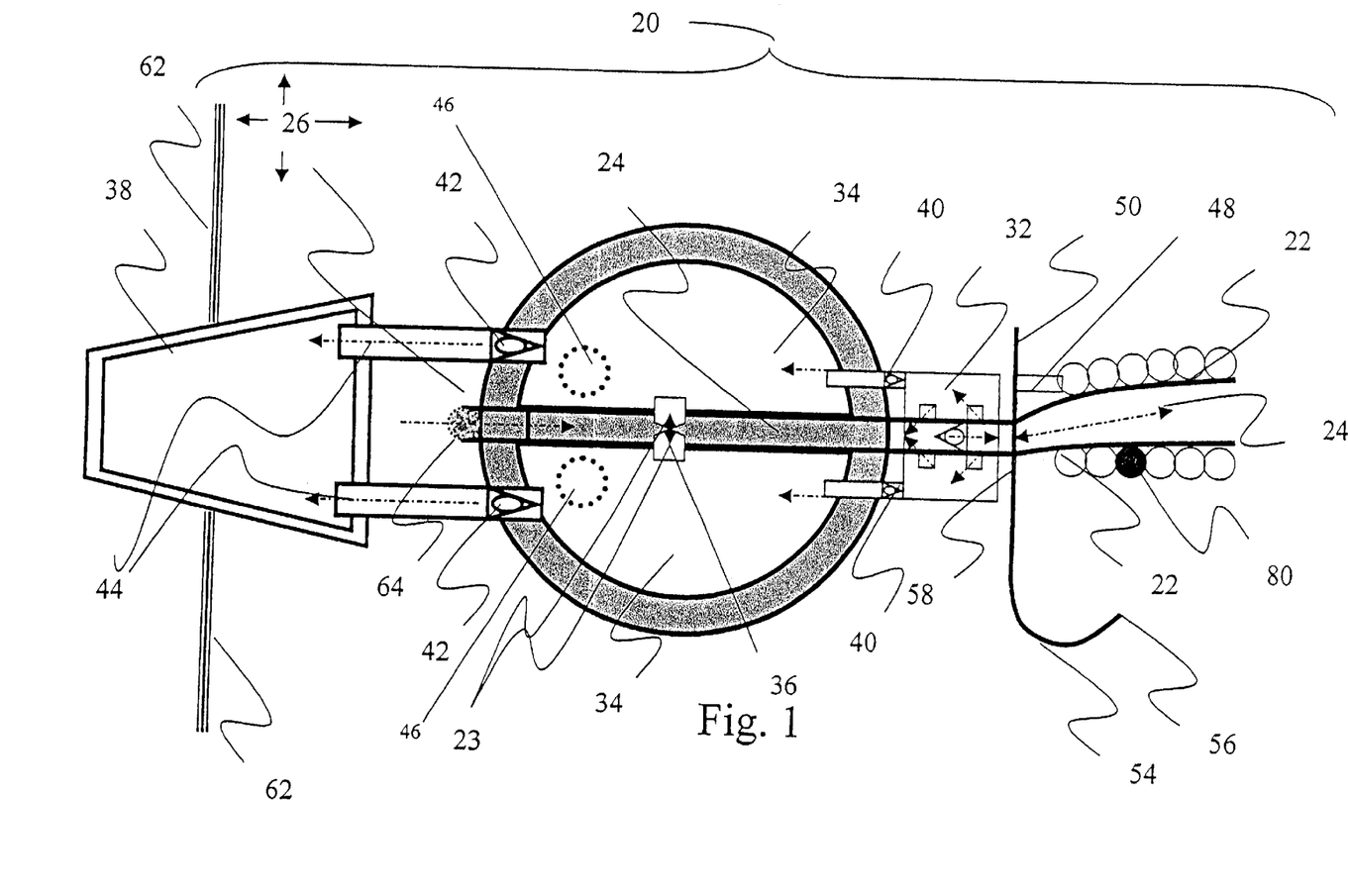
FIG. 1 is a schematic representation of a device according to the present invention.
Figure 2:
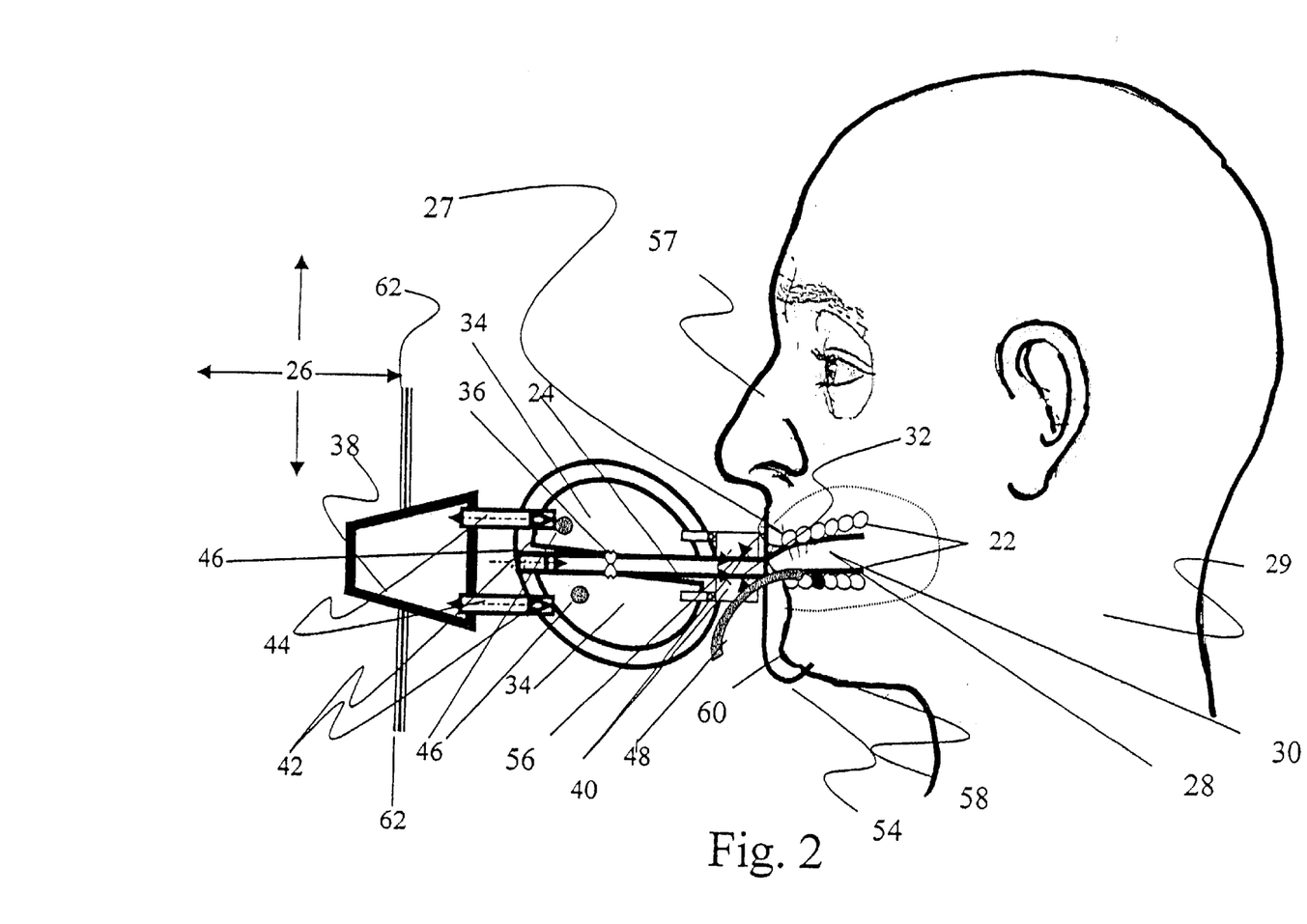
FIG. 2 depicts insertion of the device of FIG. 1 into a mouth of a patient.

Referring now to the drawings, FIG. I illustrates the self contained CPAP device 20 of the present invention. Device 20 includes a mouthpiece 22 insertable in a mouth 28 (FIG. 2) of a patient. Mouthpiece 22 may be adjustable to fit the interior 30 of mouth 28 of the patient. According to some preferred embodiments of the present invention, a mechanism for facilitating inflation 48 of mouthpiece 22 is provided. According to preferred embodiments of the present invention there is provided a mechanism for sealing 50 between mouthpiece 22 and lips 27 of the patient, such that airflow between lips 27 and mouthpiece 22 is diminished.

According to preferred embodiments of the present invention device 20 further includes a chin holder 54 having a first end 56 which is capable of engaging a chin 60 of the patient and a second end 58 which is connectable to the device.

Device 20 also includes a breathing tube 24 connecting between an outside environment 26 and an interior 30 of mouth 28. Breathing tube 24 contains at least one bidirectional pressure sensitive valve 32. Valve 32 serves to allow inhalation of air via tube 24 during inhalation, and to allow expiration of air during exhalation. Tube 24 has an internal cross sectional area 36 which changes during respiration as will be described hereinbelow. In the pictured embodiment of device 20, tube 24 has holes 23 therein.

In the pictured preferred embodiment breathing tube 24 passes through the mouthpiece to outside environment 26, although tube 24 could pass, for example between mouthpiece 22 and lips 27 without substantially effecting the function of device 20. In the pictured preferred embodiment (FIGS. 1, 2, and 3) tube 24 further includes a filter designed and constructed to prevent the entry of foreign bodies thereto.

Device 20 also includes at least one inflatable body 34 which functions to adjust internal cross sectional area 36 of breathing tube 24 during a process of respiration. Inflatable body 34 further serves to regulate an air pressure within mouth 28 during the process of respiration. The process by which this regulation occurs is detailed hereinbelow. Inflatable body 34 includes at least one elastic balloon (also labeled 34), at least one first additional unidirectional pressure sensitive valve 40 in communication an interior of breathing tube 24 and at least one second additional unidirectional pressure sensitive valve 42 in communication with an exhaled air tube 44. Exhaled air tube 44 is in communication with a mask 38. This configuration assures that exhaled air passes through pressure sensitive valve 40, thereby inflating inflatable body 34 and causing an elevated pressure to form therein and that reduction of the elevated pressure is accomplished by a release of exhaled air through pressure sensitive valve 42 into exhaled air tube 44 which directs the exhaled air to mask 38.

Inflatable body 34 may include any number of inflatable bodies (two are pictured in the drawings) having a total inflated volume which is approximately 2 to 4 ml greater than a total deflated volume thereof for each Kg of mass of said patient. For example, inflatable body 34 might have a total inflated volume which is approximately 120 to 350 ml greater than a total deflated volume thereof such that it is suitable for use in adults, or it might have a total inflated volume which is approximately 40 to 160 ml greater than a total deflated volume thereof such that it is suitable for use in children, or it might have a total inflated volume which is approximately 2 to 40 ml greater than a total deflated volume thereof such that it is suitable for use in infants.

According to some preferred embodiments of device 20, inflatable body 34 further comprises at least one unidirectional pressure sensitive safety valve 46 in communication with the outside environment 26. Safety valve 46 functions to prevent explosion of inflatable body 34 by opening to release air to outside environment 26. Safety valve 46 opens when a predetermined inflated volume is exceeded. Since inflatable body 34 will have an elevated pressure as a volume thereof increases, safety valve 46 can also be said to release exhaled air when the elevated pressure exceeds a predefined limit.

Device 20 also includes mask 38 in fluid communication with inflatable body 34 by means of exhaled air tube 44. Mask 38 is designed and constructed to cover a nose 57 of the patient, such that exhaled air is routed thereto. One ordinarily skilled in the art will be capable of modifying a commercially available mask for use,. with the present invention. Masks are available from, for example, www-.respironics.co; www.sleep-net.com; and www.sunrisemedicalonline.com.

The present invention is further embodied by a system for prophylactic treatment of a breathing disorder. The system includes a self contained CPAP device which is designed and constructed to maintain sufficient pressure in an upper airway of a patient such that collapse thereof is prevented. Self contained CPAP device functions independently of, for example, a pump, a compressor, a pressurized gas cylinder and an electro-hydrolytic oxygen source.

The present invention is further embodied by an improved method of preventing a breathing disorder by means of CPAP. The method includes at least four steps. The first step includes inserting mouthpiece 22 in mouth 28 of a patient. The second step includes allowing inhaled air to flow through at least one bi-directional pressure sensitive valve 32 contained within breathing tube 24 which connects outside environment 26 and an interior 30 of mouth 28. The third step includes adjusting internal cross sectional area 36 of breathing tube 24 during a process of respiration by means of at least one inflatable body 34 which serves to regulate an air pressure within mouth 28 during the process of respiration. The fourth step includes covering nose 57 of the patient with mask 38 which is in fluid communication with inflatable body 34 and is designed and constructed to receive exhaled air therefrom and route the exhaled air to nose 57 of the patient. The method may sometimes include the additional step of adjusting mouthpiece 22 to fit mouth 28 of the patient. This additional step may be accomplished by, for example, inflating mouthpiece 22.

According to some preferred embodiments of the present invention, device 20 further comprises at least one retaining piece 62 for holding the device in place. Retaining piece 62 may include, for example, at least one strap, at least one elastic band, at least one piece of Velcro™ or a pair of protrusions which engage the ears 59 of the patient.

Device 20 may be specifically designed and configured for many purposes including, but not limited to, treating obstructive sleep apnea, treating apnea of infancy and preventing sudden infant death syndrome.

Figure 3:
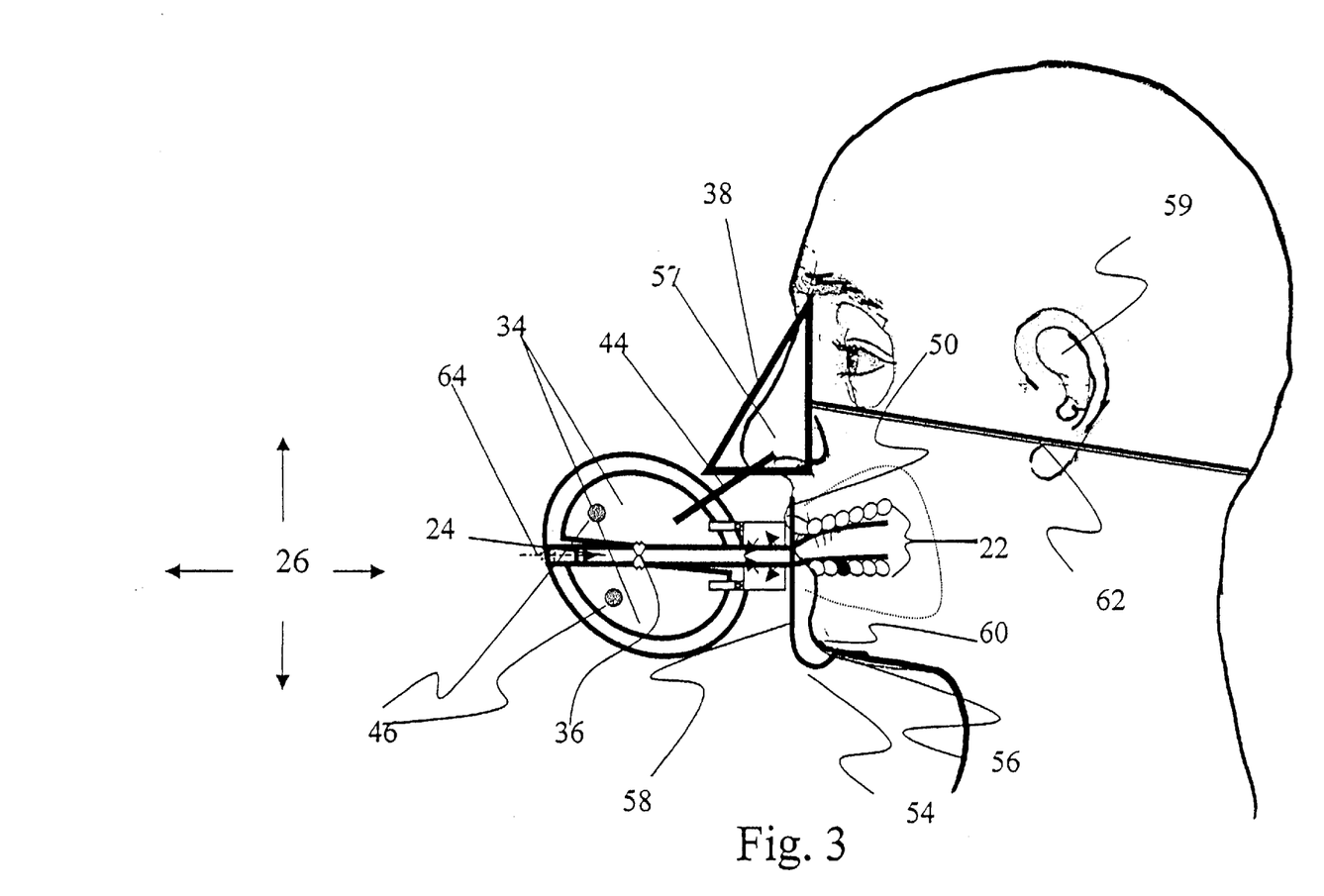
FIG. 3 depicts a device according to the present invention as in FIG. 2 with the mask covering the nose of a patient.
Figure 4A:
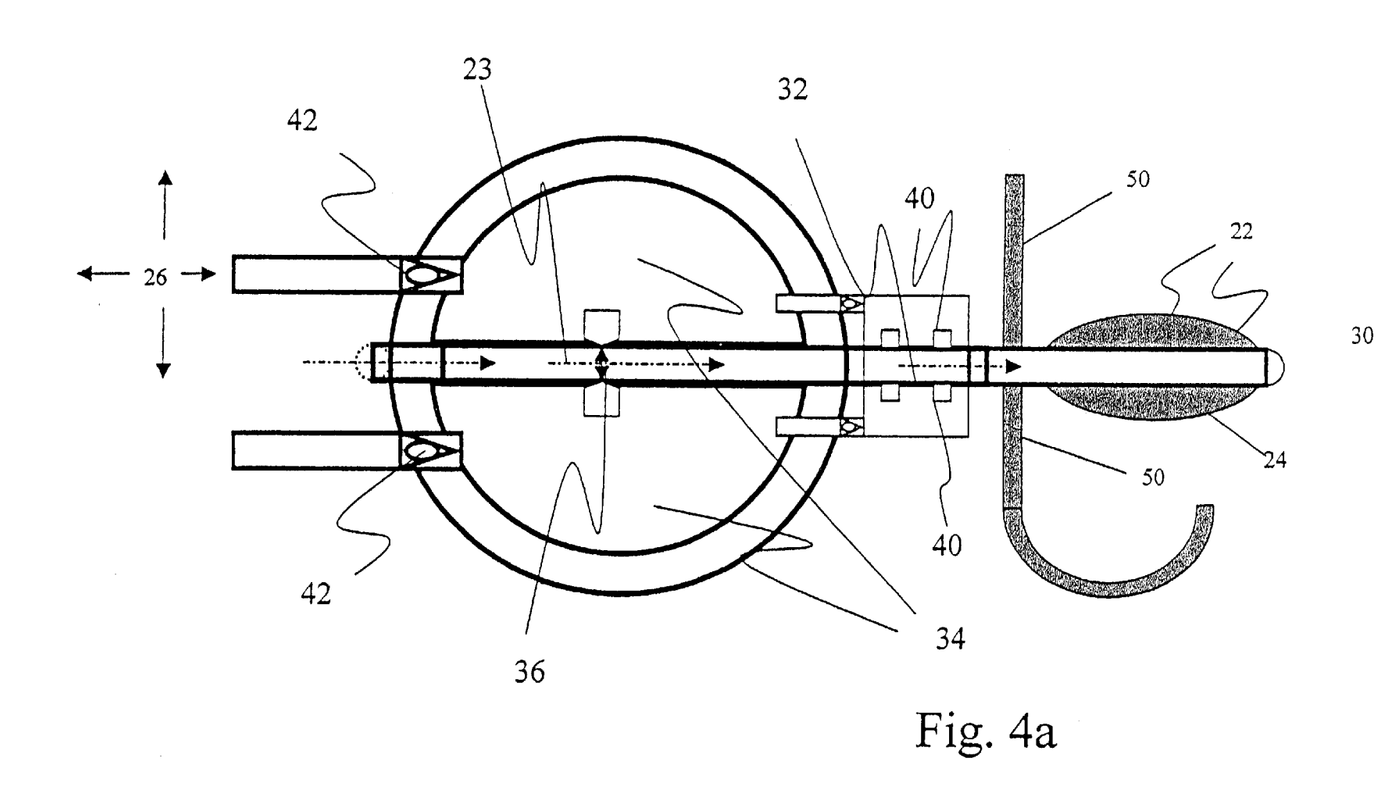

Having set forth the component parts of device 20, an explanation of their integrated function during respiration will now be provided. FIG. 4a shows the flow of air (arrows) from outside environment 26 via breathing tube 24 with internal cross sectional area 36 into interior of the mouth 30 during the first inhalation of a patient that has assembled device 20 on their face (as shown in FIG. 3). Flow of air through valve 32 is inward towards mouthpiece 22. Valve 32 opens at a very low pressure in this direction, for example 1 cm of H$_2$O or less. There is no flow of air at this stage through valves 40 and 42. Inflatable bodies 34 do not protrude through holes 23 because they are not yet inflated.

Figure 4B:
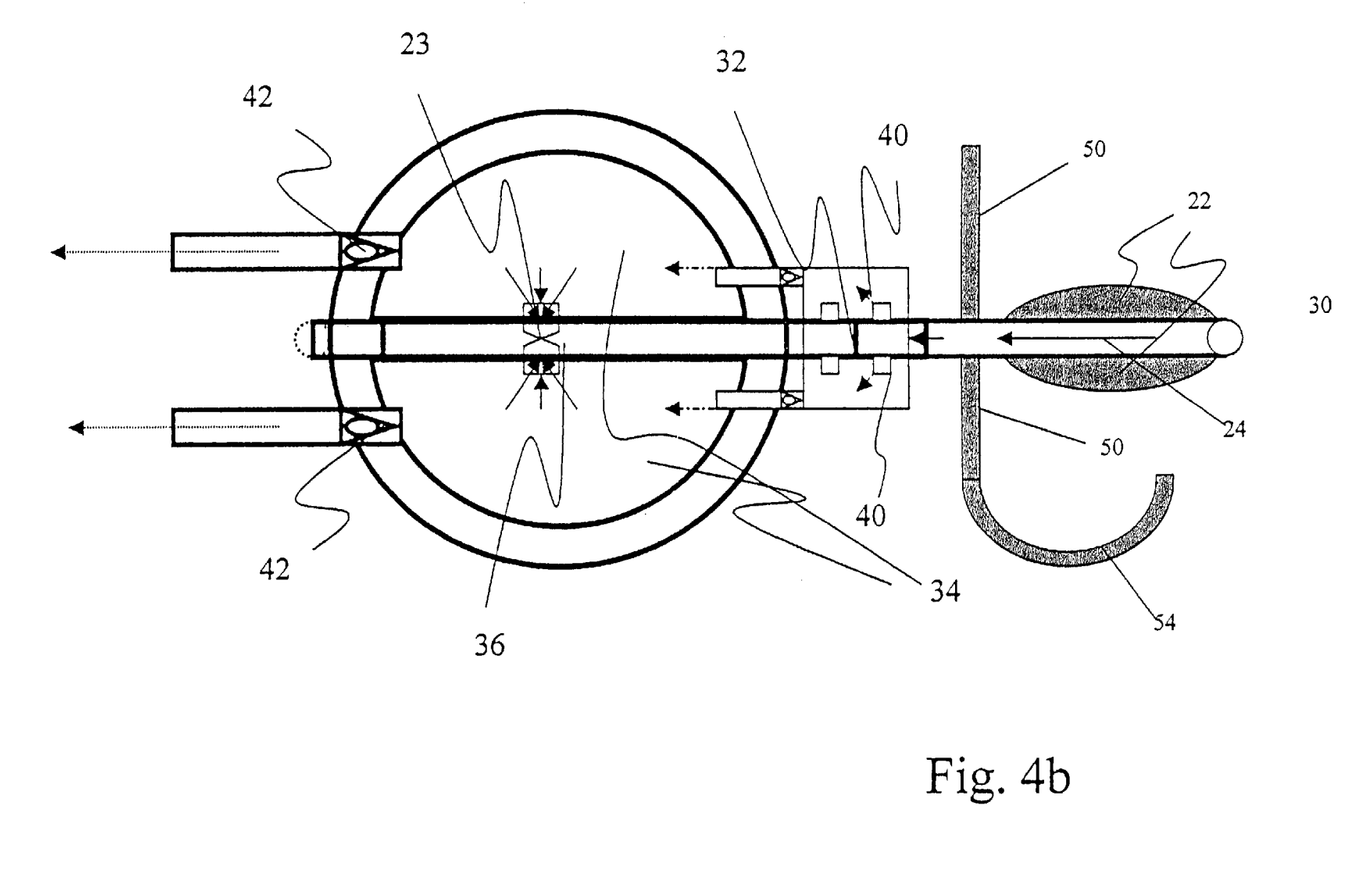

FIG. 4b shows the flow of air (arrows) during exhalation. Airflows outward from interior of mouth 30 via breathing tube 24 towards unidirectional valves 40 and bidirectional valve 32. Valves 40 open at a lower pressure than valve 32 so that exhaled airflows primarily into inflatable body 34 which begins to protrude through holes 23 in tube 24 as it expands, thereby reducing cross sectional area 36 of tube 24. Reduction of cross sectional area 36 of tube 24 is significant, for example reduced area 36 may be as little as one quarter or one eighth of initial area 36. As pressure within inflatable body 34 increases, valves 42, which communicate with exhaled air tube 44 (FIGS. 1,2, and 3) open. This establishes a flow of air under slight positive pressure through nose 57 into interior of mouth 30 and subglottal region 29 of the airway. The positive pressure is preferably in excess of 12 cm of water, more preferably between 12 and 40 cm of water and most preferably approximately exactly 40 cm of water. This pressure also causes inflatable body 34 to expand through holes 23 in tube 24 thereby reducing cross sectional area 36 thereof. Approximately 300 ml of pressurized exhaled air collects in inflatable body 34 during exhalation. Because inflatable body 34 is elastic, this air continues to flow outward through valves 42 after exhalation ceases. Because valves 40 are unidirectional, air does not flow back into tube 24 from inflatable body 34. During exhalation, outward airflow through bi-directional valve 32 is partially obstructed because inflatable body 34 reduces cross sectional area 36 of tube 24 significantly as explained hereinabove. Inflatable body 34 also compresses partially elastic bi-directional valve 32 in order to allow some exhaled air to flow through tube 24 to outside environment 26.

Figure 4C:
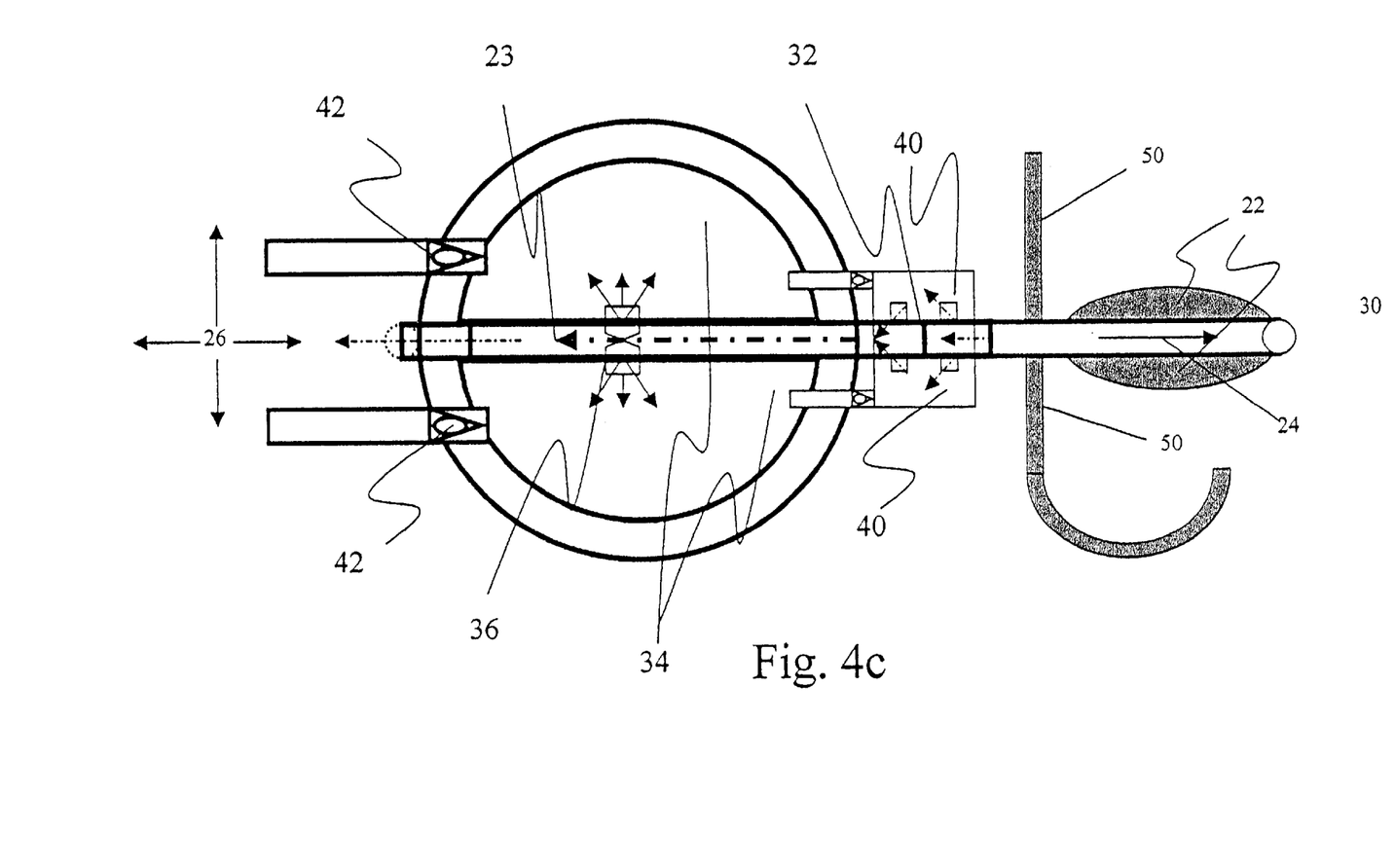

During subsequent inhalations (FIG. 4c), air continues to flow outward through valves 42 maintaining positive pressure in the subglottal region 29 of the upper airway as described hereinabove. This outward flow reduces the volume of inflatable body 34 which tends to withdraw from holes 23 in tube 24 thereby increasing cross sectional area 36. Airflow during subsequent inhalations is otherwise as described for the first inhalation hereinabove.

Function of device 20 as described hereinabove is dependent to a large degree upon pressure differentials for operation of valves 32 and 40 and for operation of valves 40 and 42. In general, a pressure difference of 1 cm of water for each of these pairs should be sufficient to facilitate operation of device 20. One ordinarily skilled in the art will be able to assemble device 20 using commercially available valves from, for example, Hans Rudolph Inc. (Kansas City, Mo., USA). Valves 42 may be, in some preferred embodiments, two stage valves, such that inhalation via nose 57 is required to initiate release of exhaled air from inflatable body 34 via valves 42.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A system for prophylactic treatment of a breathing disorder, the system comprising a self contained CPAP device, said device being designed and constructed to:

(a) maintain sufficient pressure in an upper airway of a patient such that collapse thereof is prevented; and (b) function independently of any item selected from the group consisting of a pump, a compressor, a pressurized gas cylinder and an electro-hydrolytic oxygen source;

wherein said device comprises:
- (i) a mouthpiece insertable in a mouth of said patient;
- (ii) a breathing tube connecting between an outside environment and an interior of said mouth, said breathing tube containing at least one bi-directional pressure sensitive valve therein;
- (iii) at least one inflatable body, said at least one inflatable body functioning to adjust an internal cross sectional area of said breathing tube during a process of respiration, said at least one inflatable body further serving to regulate an air pressure within said mouth during said process of respiration; and
- (iv) a mask, said mask being in fluid communication with said at least one inflatable body and being designed and constructed to cover a nose of said patient, such that exhaled air is routed thereto.

2. The system of claim 1, wherein said at least one inflatable body comprises:
- (1) at least one elastic balloon;
- (2) at least one first additional pressure sensitive valve in communication an interior, of said breathing tube; and
- (3) at least one second additional pressure sensitive valve in communication with an exhaled air tube said exhaled air tube being in communication with said mask;

wherein said additional pressure sensitive valves are unidirectional.

3. The system of claim 2, further comprising:
- (4) at least one unidirectional pressure sensitive safety valve in communication with said outside environment, said safety valve functioning to prevent explosion of said at least one inflatable body.

4. The system of claim 3, wherein said safety valve opens when a predetermined volume is exceeded.

5. The system of claim 1, wherein said at least one inflatable body comprises any number of inflatable bodies having a total inflated volume which is approximately 120 to 350 ml greater than a total deflated volume thereof such that it is suitable for use in adults.

6. The system of claim 1, wherein said at least one inflatable body comprises any number of inflatable bodies having a total inflated volume which is approximately 40 to 160 ml greater than a total deflated volume thereof such that it is suitable for use in children.

7. The system of claim 1, wherein said at least one inflatable body comprises any number of inflatable bodies having a total inflated volume which is approximately 2 to 40 ml greater than a total deflated volume thereof such that it is suitable for use in infants.

8. The system of claim 1, wherein said at least one inflatable body comprises any number of inflatable bodies having a total inflated volume which is approximately 2 to 4 ml greater than a total deflated volume thereof for each Kg of mass of said patient.

9. The system of claim 1, wherein said mouthpiece is adjustable to fit said mouth of said patient.

10. The system of claim 9, further comprising a mechanism for facilitating inflation of said mouthpiece.

11. The system of claim 1, further comprising a mechanism for seating between said mouthpiece and lips of said patient, such that airflow between said lips and said mouthpiece is diminished.

12. The system of claim 1, further comprising a chin holder having a first end which is capable of engaging a chin of said patient and a second end which is connectable to the device.

13. The system of claim 1, wherein said breathing tube passes through said mouthpiece.

14. The system of claim 1, further comprising at least one retaining piece for holding the device in place.

15. The system of claim 14, wherein said at least one retaining piece includes at least one item selected from the group consisting of at least one strap, at least one elastic band, at least one piece of Velcro™ and a pair of protrusions which engage the ears of said patient.

16. The system of claim 1, further comprising a filter in said breathing tube, said filter designed and constructed to prevent the entry of foreign bodies thereto.

17. The system of claim 1, wherein said breathing disorder is selected from the group consisting of obstructive sleep apnea, apnea of infancy, and sudden infant death syndrome.

18. An improved method of preventing a breathing disorder by means of CPAP, the method comprising the steps of:
- (a) inserting a mouthpiece in a mouth of a patient;
- (b) allowing inhaled air to flow through at least one bi-directional pressure sensitive valve contained within a breathing tube connecting between an outside environment and an interior of said mouth;
- (c) adjusting an internal cross sectional area of said breathing tube during a process of respiration by means of at least one inflatable body, said at least one inflatable body serving to regulate an air pressure within said mouth during said process of respiration; and
- (d) covering a nose of said patient with a mask, said mask being in fluid communication with said at least one inflatable body and being designed and constructed to receive exhaled air therefrom and route said exhaled air to said nose of said patient.

19. The method of claim 18, wherein said at least one inflatable body comprises:
- (i) at least one elastic balloon;
- (ii) at least one first additional pressure sensitive valve in communication an interior of said breathing tube; and
- (iv) at least one second additional pressure sensitive valve in communication with an exhaled air tube, said exhaled air, tube being in communication with said mask;

wherein exhaled air passes through said first additional pressure sensitive valve, thereby inflating said at least one inflatable body and causing an elevated pressure to form therein; and wherein reducing of said elevated pressure is accomplished by a release of exhaled air through said second additional pressure sensitive valve; and wherein said additional pressure sensitive valves are unidirectional.

20. The method of claim 19, further comprising:
- (iv) at least one unidirectional pressure sensitive safety valve in communication with said outside environment, wherein exploding of said at least one inflatable body is prevented by release of said exhaled air through said safety valve when said elevated pressure exceeds a predefined limit.

21. The method of claim 20, wherein said safety valve opens when a predetermined volume is exceeded.

22. The method of claim 18, wherein said at least one inflatable body comprises any number of inflatable bodies having a total inflated volume which is approximately 120 to 350 ml greater than a total deflated volume thereof such that it is suitable for use in adults.

23. The method of claim 18, wherein said at least one inflatable body comprises any number of inflatable bodies having a total inflated volume which is approximately 40 to 160 ml greater than a total deflated volume thereof such that it is suitable for use in children.

24. The method of claim 18, wherein said at least one inflatable body comprises any number of inflatable bodies having a total inflated volume which is approximately 2 to 40 ml greater than a total deflated volume thereof such that it is suitable for use in infants.

25. The method of claim 18, wherein said at least one inflatable body comprises any number of inflatable bodies having a total inflated volume which is approximately 2 to 4 ml greater than a total deflated volume thereof for each Kg of mass of said patient.

26. The method of claim 18, comprising the additional step of adjusting said mouthpiece to fit said mouth of said patient.

27. The method of claim 26, wherein said step of adjusting is accomplished by inflating said mouthpiece.

28. The method of claim 18, comprising the additional step of sealing between said mouthpiece and lips of said patient, such that airflow between said lips and said mouthpiece is diminished.

29. The method of claim 18, comprising the additional steps of engaging a chin of said patient with a first end of a chin holder and connecting a second end of said chin holder to an item selected from the group consisting of said mouthpiece, said breathing tube, said at least one inflatable body and said mask.

30. The method of claim 18, wherein said breathing tube passes through said mouthpiece.

31. The method of claim 18, comprising the additional step of providing at least one retaining piece for holding said mouthpiece in place.

32. The method of claim 31, wherein said at least one retaining piece includes at least one item selected from the group consisting of at least one strap, at least one elastic band, at least one piece of Velcro™ and a pair of protrusions which engage the ears of said patient.

33. The method of claim 18, comprising the additional step of providing a filter in said breathing tube, said filter designed and constructed to prevent the entry of foreign bodies thereto.

34. The method of claim 18, wherein the breathing disorder is selected from the group consisting of obstructive sleep apnea, apnea of infancy and sudden infant death syndrome.

* * * * *